(12) United States Patent
Lee et al.

(10) Patent No.: US 10,532,209 B2
(45) Date of Patent: *Jan. 14, 2020

(54) COCHLEAR IMPLANTS HAVING MRI-COMPATIBLE MAGNET APPARATUS AND ASSOCIATED METHODS

(71) Applicant: ADVANCED BIONICS AG, Staefa (CH)

(72) Inventors: Sung Jin Lee, Valencia, CA (US); Jeryle L. Walter, Valencia, CA (US); James George Elcoate Smith, Santa Clarita, CA (US); Uli Gommel, Valencia, CA (US); Stephanie M. Reed, Conshohocken, PA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/060,383

(22) PCT Filed: Dec. 18, 2015

(86) PCT No.: PCT/US2015/066851
§ 371 (c)(1),
(2) Date: Jun. 7, 2018

(87) PCT Pub. No.: WO2017/105510
PCT Pub. Date: Jun. 22, 2017

(65) Prior Publication Data
US 2018/0369586 A1 Dec. 27, 2018

(51) Int. Cl.
*A61N 1/00* (2006.01)
*A61N 1/36* (2006.01)
(Continued)

(52) U.S. Cl.
CPC .......... *A61N 1/36038* (2017.08); *A61N 1/08* (2013.01); *A61N 1/36036* (2017.08);
(Continued)

(58) Field of Classification Search
CPC .... A61N 1/0541; A61N 1/36; A61N 1/36032; A61N 1/36038; A61N 1/37223;
(Continued)

(56) References Cited

U.S. PATENT DOCUMENTS 4,352,960 A 10/1982 Dormer et al.
4,595,390 A 6/1986 Hakim et al.
(Continued)

FOREIGN PATENT DOCUMENTS

EP 2117489 B1 5/2010
EP 2853287 A1 4/2015
(Continued)

OTHER PUBLICATIONS

U.S. Appl. No. 15/568,470, filed Oct. 21, 2017, 20180110986A1.
(Continued)

*Primary Examiner* — Mallika D Fairchild
(74) *Attorney, Agent, or Firm* — Henricks Slavin LLP

(57) ABSTRACT

A cochlear implant including a cochlear lead, an antenna, a stimulation processor, and a magnet apparatus, associated with the antenna, including a case defining a central axis, a magnet frame within the case and rotatable about the central axis of the case, and a plurality of diametrically magnetized magnets that are located in the magnet frame, the magnets defining a longitudinal axis and a N-S direction and being rotatable about the longitudinal axis relative to the magnet frame and biased by the magnet frame to a predetermined N-S rotational orientation.

19 Claims, 9 Drawing Sheets

(51) Int. Cl.
*A61N 1/375* (2006.01)
*A61N 1/08* (2006.01)
*H04R 25/00* (2006.01)

(52) U.S. Cl.
CPC ........... *A61N 1/375* (2013.01); *H04R 25/606* (2013.01); *H04R 2225/67* (2013.01)

(58) Field of Classification Search
CPC .. A61N 1/37229; A61N 1/3758; A61N 1/375; A61N 1/37217; A61N 1/08; A61N 1/36036
See application file for complete search history.

(56) References Cited

U.S. PATENT DOCUMENTS

| | | |
|---|---|---|
| 4,606,329 A | 8/1986 | Hough |
| 4,618,949 A | 10/1986 | Lister |
| RE32,947 E | 6/1989 | Dormer et al. |
| 5,290,281 A | 3/1994 | Tschakaloff |
| 5,755,762 A | 5/1998 | Bush |
| 5,824,022 A | 10/1998 | Zilberman et al. |
| 5,945,762 A | 8/1999 | Chen et al. |
| 6,178,353 B1 | 1/2001 | Griffith et al. |
| 6,190,305 B1 | 2/2001 | Ball et al. |
| 6,217,508 B1 | 4/2001 | Ball et al. |
| 6,227,820 B1 | 5/2001 | Jarvik |
| 6,292,678 B1 | 9/2001 | Hall et al. |
| 6,348,070 B1 | 2/2002 | Teissl et al. |
| 6,358,281 B1 | 3/2002 | Berrang et al. |
| 6,599,321 B2 | 7/2003 | Hyde, Jr. |
| 6,838,963 B2 | 1/2005 | Zimmerling |
| 7,091,806 B2 | 8/2006 | Zimmerling et al. |
| 7,190,247 B2 | 3/2007 | Zimmerling |
| 7,566,296 B2 | 7/2009 | Zimmerling et al. |
| 7,609,061 B2 | 10/2009 | Hochmair |
| 7,642,887 B2 | 1/2010 | Zimmerling |
| 7,680,525 B1 | 3/2010 | Damadian |
| 7,774,069 B2 | 8/2010 | Olson et al. |
| 7,856,986 B2 | 12/2010 | Darley |
| 7,881,800 B2 | 2/2011 | Daly et al. |
| 7,976,453 B2 | 7/2011 | Zimmerling et al. |
| 8,013,699 B2 | 9/2011 | Zimmerling |
| 8,118,725 B2 | 2/2012 | Zimmerling et al. |
| 8,255,058 B2 | 8/2012 | Gibson et al. |
| 8,340,774 B2 | 12/2012 | Hochmair et al. |
| 8,634,909 B2 | 1/2014 | Zimmerling et al. |
| 8,733,494 B1 | 5/2014 | Leigh |
| 8,734,475 B2 | 5/2014 | Ekvall et al. |
| 8,744,106 B2 | 6/2014 | Ball |
| 8,758,394 B2 | 6/2014 | Zimmerling et al. |
| 8,787,608 B2 | 7/2014 | Van Himbeeck et al. |
| 8,790,409 B2 | 7/2014 | Van den Heuvel et al. |
| 8,825,171 B1 | 9/2014 | Thenuwara et al. |
| 8,891,795 B2 | 11/2014 | Andersson |
| 8,897,475 B2 | 11/2014 | Ball et al. |
| RE45,701 E | 9/2015 | Zimmerling et al. |
| 9,126,010 B2 | 9/2015 | Shah et al. |
| 9,162,054 B2 | 10/2015 | Dalton |
| 9,227,064 B2 | 1/2016 | Duftner |
| 9,295,425 B2 | 3/2016 | Ball |
| 9,314,625 B2 | 4/2016 | Kasic, II et al. |
| 9,352,149 B2 | 5/2016 | Thenuwara et al. |
| RE46,057 E | 7/2016 | Zimmerling et al. |
| 9,392,382 B2 | 7/2016 | Nagl et al. |
| 9,420,388 B2 | 8/2016 | Ball |
| 9,549,267 B2 | 1/2017 | Nagl et al. |
| 9,615,181 B2 | 4/2017 | Nagl et al. |
| 9,656,065 B2 | 5/2017 | Tourrel et al. |
| 9,919,154 B2 | 3/2018 | Lee |
| 9,931,501 B2 | 4/2018 | Smyth |
| 10,300,276 B2 | 5/2019 | Lee et al. |
| 10,463,849 B2 | 11/2019 | Lee et al. |
| 2004/0012470 A1 | 1/2004 | Zimmerling et al. |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2006/0244560 A1 | 11/2006 | Zimmerling et al. |
| 2007/0053536 A1 | 3/2007 | Westerkull |
| 2007/0126540 A1 | 6/2007 | Zimmerling |
| 2008/0103350 A1 | 5/2008 | Farone |
| 2008/0195178 A1 | 8/2008 | Kuzma |
| 2009/0048580 A1 | 2/2009 | Gibson |
| 2009/0099403 A1 | 4/2009 | Zimmerling et al. |
| 2009/0134721 A1 | 5/2009 | Zimmerling |
| 2009/0248155 A1 | 10/2009 | Parker |
| 2009/0287278 A1 | 11/2009 | Charvin |
| 2010/0004716 A1 | 1/2010 | Zimmerling et al. |
| 2010/0046778 A1 | 2/2010 | Crawford et al. |
| 2010/0046779 A1 | 2/2010 | Crawford et al. |
| 2011/0009925 A1 | 1/2011 | Leigh et al. |
| 2011/0022120 A1 | 1/2011 | Ball et al. |
| 2011/0068885 A1 | 3/2011 | Fullerton et al. |
| 2011/0218605 A1 | 9/2011 | Cryer |
| 2011/0224756 A1 | 9/2011 | Zimmerling et al. |
| 2011/0255731 A1 | 10/2011 | Ball |
| 2011/0264172 A1 | 10/2011 | Zimmerling et al. |
| 2012/0296155 A1 | 11/2012 | Ball |
| 2013/0079749 A1 | 3/2013 | Overstreet et al. |
| 2013/0184804 A1 | 7/2013 | Dalton |
| 2013/0343588 A1 | 12/2013 | Karunasiri |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121449 A1 | 5/2014 | Kasic et al. |
| 2014/0121586 A1 | 5/2014 | Bertrand et al. |
| 2014/0163692 A1 | 6/2014 | Van den Heuvel et al. |
| 2014/0343626 A1 | 11/2014 | Thenuwara et al. |
| 2015/0025613 A1 | 1/2015 | Nyberg, II et al. |
| 2015/0073205 A1 | 3/2015 | Ball et al. |
| 2015/0087892 A1 | 3/2015 | Tourrel et al. |
| 2015/0100109 A1 | 4/2015 | Feldman et al. |
| 2015/0265842 A1 | 9/2015 | Ridler |
| 2015/0367126 A1 | 12/2015 | Smyth |
| 2015/0382114 A1 | 12/2015 | Andersson et al. |
| 2016/0037273 A1 | 2/2016 | Gustafsson |
| 2016/0144170 A1 | 5/2016 | Gibson et al. |
| 2016/0205484 A1 | 7/2016 | Nagl et al. |
| 2016/0310737 A1 | 10/2016 | Tourrel et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0050027 A1 | 2/2017 | Andersson et al. |
| 2017/0078808 A1 | 3/2017 | Kennes |
| 2017/0156010 A1 | 6/2017 | Verma et al. |
| 2017/0239476 A1 | 8/2017 | Lee et al. |
| 2018/0028818 A1 | 2/2018 | Andersson et al. |
| 2018/0110985 A1 | 4/2018 | Walter |
| 2018/0110986 A1 | 4/2018 | Lee |
| 2018/0133486 A1 | 5/2018 | Smith |
| 2018/0185634 A1 | 7/2018 | Smyth |
| 2018/0296826 A1 | 10/2018 | Lee et al. |
| 2018/0304078 A1 | 10/2018 | Crawford et al. |
| 2019/0046797 A1 | 2/2019 | Calixto et al. |
| 2019/0076649 A1 | 3/2019 | Lee et al. |
| 2019/0255316 A1 | 8/2019 | Lee et al. |

FOREIGN PATENT DOCUMENTS

| | | |
|---|---|---|
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |

(56) References Cited

FOREIGN PATENT DOCUMENTS

| WO | WO2010083554 A1 | 7/2010 |
|---|---|---|
| WO | WO2011011409 A1 | 1/2011 |
| WO | WO2011109486 A2 | 9/2011 |
| WO | WO2011133747 A1 | 10/2011 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |
| WO | WO2016190886 A1 | 12/2016 |
| WO | WO2016191429 A1 | 12/2016 |
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105511 A1 | 6/2017 |
| WO | WO2017105604 A1 | 6/2017 |
| WO | WO2017172566 A1 | 10/2017 |
| WO | WO2018190813 A1 | 10/2018 |
| WO | WO2018191314 A1 | 10/2018 |
| WO | WO2018199936 A1 | 11/2018 |

OTHER PUBLICATIONS

U.S. Appl. No. 15/703,808, filed Sep. 13, 2017.
PCT International Search and Written Opinion dated Sep. 19, 2016 for PCT App. U.S. Appl. No. PCT/US2015/066851.
Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.
Teissl et al., "Magentic Resonance Imagiing and Cochlear Imlants: Compatibility and Safety Aspects," Journal of Magnetic Resonance Imaging, Society for Magnetic Resonance Imaging, vol. 9, No. 1, pp. 26-38, Jan. 1, 1999.
U.S. Appl. No. 15/568,469, filed Oct. 21, 2017, 20180110985A1.
U.S. Appl. No. 15/770,207, filed Apr. 22, 2018, 20180304078 A1.
U.S. Appl. No. 16/060,383, filed Jun. 7, 2018, 20180369586 A1.
U.S. Appl. No. 15/591,054, filed May 9, 2017, U.S. Pat. No. 9,919,154.
U.S. Appl. No. 16/009,600, filed Jun. 15, 2018, 20180296826A1.
U.S. Appl. No. 16/403,582, filed May 5, 2019.
U.S. Appl. No. 15/568,470, filed Oct. 21, 2017, U.S. Pat. No. 10,300,276.
U.S. Appl. No. 16/101,390, filed Aug. 10, 2018, 20190046797 A1.
U.S. Appl. No. 15/703,808, filed Sep. 13, 2017, 20190076649 A1.
U.S. Appl. No. 15/805,025, filed Nov. 6, 2017, 20180133486 A1.
U.S. Appl. No. 15/568,469, filed Oct. 21, 2017, U.S. Pub. Pat. No. 20180110985A1.
U.S. Appl. No. 15/770,207, filed Apr. 22, 2018, U.S. Pub. Pat. No. 20180304078 A1.
U.S. Appl. No. 16/060,383, filed Jul. 7, 2018, U.S. Pub. Pat. No. 20180369586 A1.
U.S. Appl. No. 15/591,054, filed May 9, 2017, U.S. Pub. Pat. No. 9919154.
U.S. Appl. No. 16/009,600, filed Jul. 15, 2018, U.S. Pub. Pat. No. 20180296826A1.
U.S. Appl. No. 16/403,582, filed May 5, 2019, U.S. Pub. Pat. No. 20190255316A1.
U.S. Appl. No. 15/568,470, filed Oct. 21, 2017, U.S. Pub. Pat. No. 10,300,276.
U.S. Appl. No. 16/101,390, filed Aug. 10, 2018, U.S. Pub. Pat. No. 20190046797 A1.
U.S. Appl. No. 15/703,808, filed Sep. 13, 2017, U.S. Pub. Pat. No. 20190076649 A1.
U.S. Appl. No. 15/805,025, filed Nov. 6, 2017, U.S. Pub. Pat. No. 20180133486 A1.
U.S. Appl. No. 16/499,311, filed Sep. 29, 2019.
U.S. Appl. No. 16/603,868, filed Oct. 29, 2019.

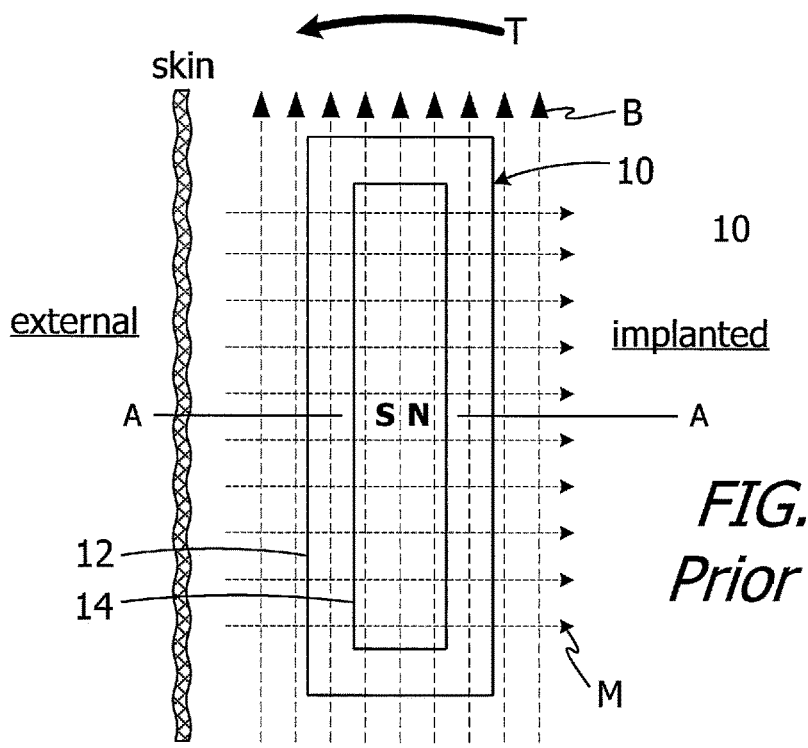
FIG. 1
Prior Art
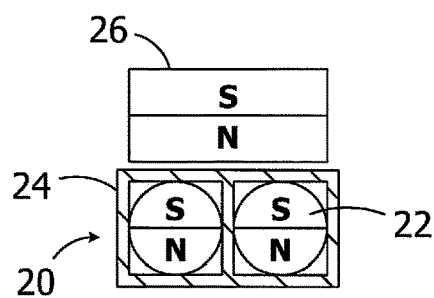
FIG. 2 - Prior Art
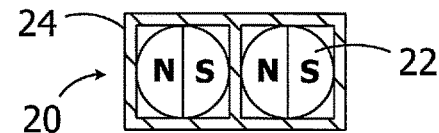
FIG. 3
Prior Art
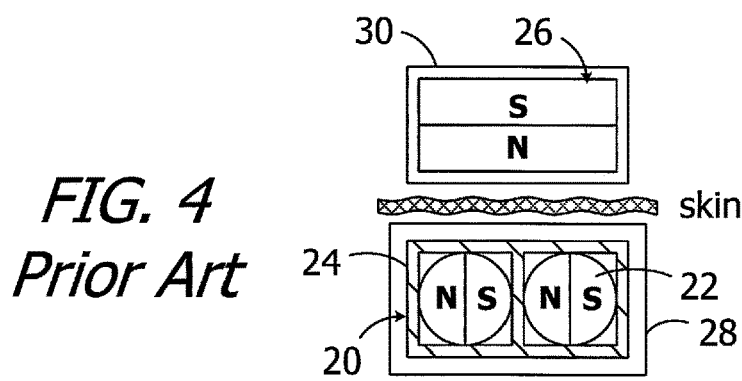
FIG. 4
Prior Art

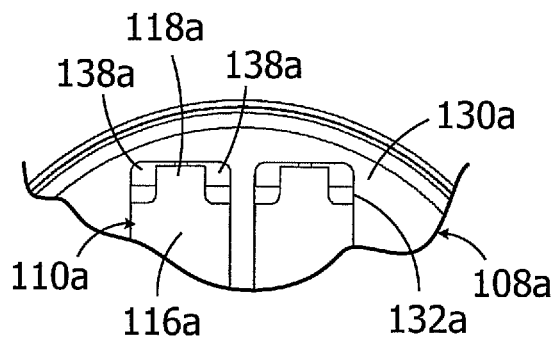
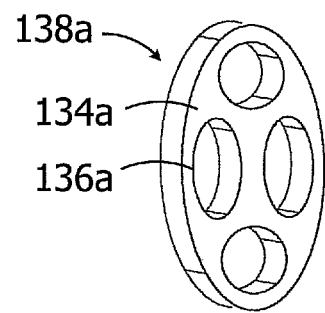
FIG. 20        FIG. 21
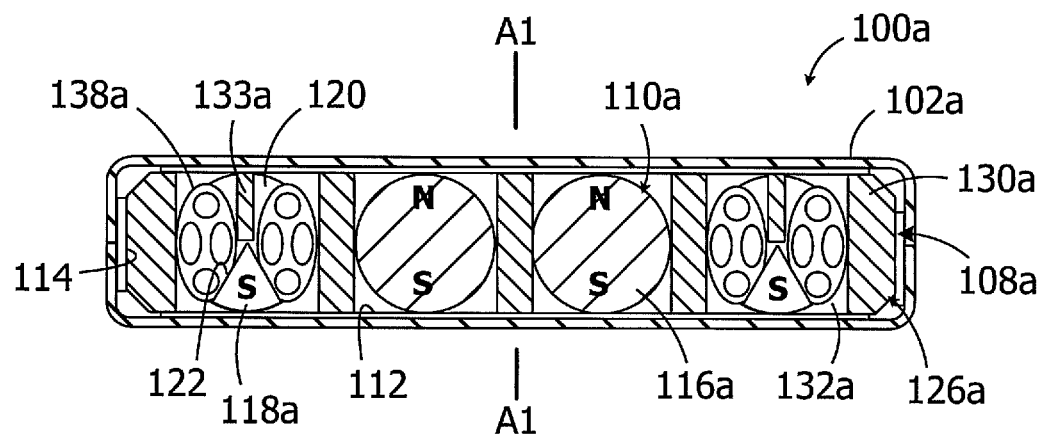
FIG. 22

COCHLEAR IMPLANTS HAVING MRI-COMPATIBLE MAGNET APPARATUS AND ASSOCIATED METHODS

CROSS-REFERENCE TO RELATED APPLICATIONS

This application is the U.S. National Stage of PCT App. Ser. No. PCT/US2015/066851, filed Dec. 18, 2015.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics Harmony™ BTE sound processor, the Advanced Bionics Naida CI Q Series BTE sound processors and the Advanced Bionics Neptune™ body worn sound processor.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing.

The present inventors have determined that conventional cochlear implants are susceptible to improvement. For example, the magnets in many conventional cochlear implants are disk-shaped and have north and south magnetic dipoles that are aligned in the axial direction of the disk. Such magnets are not compatible with magnetic resonance imaging ("MRI") systems. In particular, the cochlear implant 10 illustrated in FIG. 1 includes, among other things, a housing 12 and a disk-shaped solid block magnet 14. The implant magnet produces a magnetic field M in a direction that is perpendicular to the patient's skin and parallel to the axis A, and this magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may demagnetize the implant magnet 14 or generate a significant amount of torque T on the implant magnet 14. The torque T may dislodge the implant magnet 14 from the pocket within the housing 12, reverse the magnet 14 and/or dislocate the cochlear implant 10, all of which may also induce tissue damage. One proposed solution involves surgically removing the implant magnet 14 prior to the MRI procedure and then surgically replacing the implant magnet thereafter.

One proposed solution involves the use of freely rotatable ball magnets that create a magnetic field which can rotate, from the aforementioned direction that is perpendicular to the patient's skin, to a direction that is aligned with the direction of the MRI magnetic field B. To that end, and referring to FIG. 2, one proposed implantable magnet apparatus 20 includes a plurality of freely rotatable ball magnets 22 within a case 24. When the magnet apparatus 20 is in very close proximity to an external magnet 26, the ball magnets 22 will align with the external magnet 26 in the manner shown, with the N-S direction of the ball magnets being the same as that of the external magnet. When the external magnet 26 is removed (FIG. 3), the ball magnets 22 will align with one another. The ball magnets 22 will then rotate as necessary in response to the application of the MRI magnetic field, thereby minimizing the torque T, because the MRI magnetic field is far stronger than the attraction between the ball magnets. Turning to FIG. 4, the present inventors have determined that the use of freely rotatable ball magnets 22 is less than optimal because the distance between implanted ball magnets (located within a cochlear implant 28) and the external magnet 26 (located within an external headpiece 30) is so great that the magnetic attraction between the ball magnets is greater than the magnetic attraction between the ball magnets and the external magnet. The N-S direction of the ball magnets 22 is perpendicular to the N-S direction of the external magnet 26. The increased distance, as compared to the distance illustrated in FIG. 2, is a product of, for example, the presence of the implant and headpiece housings and the thickness of the skin flap. The weak magnetic attraction resulting from the misalignment of the magnetic fields prevents the headpiece from properly mounting to the patient's head. One possible solution is to simply increase the size of the external magnet, thereby increasing the strength of the associated magnetic field to the point at which the ball magnets 22 in a cochlear implant will rotate into the orientation illustrated in FIG. 2. The present inventors have determined, however, that the associated increase in the size and weight of the headpiece is undesirable.

SUMMARY

A cochlear implant in accordance with one of the present inventions includes a cochlear lead, an antenna, a stimulation processor, a magnet apparatus, associated with the antenna, including a case defining a central axis, a magnet frame within the case and rotatable about the central axis of the case, and a plurality of diametrically magnetized magnets that are located in the magnet frame, the magnets defining a longitudinal axis and a N-S direction and being rotatable about the longitudinal axis relative to the magnet frame and biased by the magnet frame to a predetermined N-S rotational orientation. The present inventions also include systems with such a cochlear implant in combination with a sound processor and a headpiece.

A method in accordance with one of the present inventions may be practiced in conjunction with an implantable cochlear stimulator including an antenna and a magnet apparatus, associated with the antenna, having a case that defines a central axis, a magnet frame within the case and rotatable about the central axis of the case, and a plurality of diametrically magnetized magnets that define a longitudinal axis and a N-S direction and are located in the magnet frame and rotatable about the longitudinal axis relative to the magnet frame. The method includes the step of biasing the magnets to a predetermined N-S rotational orientation where the N-S directions are not perpendicular to the central axis of the case.

There are a number of advantages associated with such apparatus and methods. For example, a strong magnetic field, such as an MRI magnetic field, will not demagnetize the magnet apparatus. Nor will it generate a significant amount of torque on the magnet apparatus and associated cochlear implant. As a result, surgical removal of the cochlear implant magnet prior to an MRI procedure, and then surgically replacement thereafter, is not required. Moreover, in the absence of the strong magnetic field, the magnetic attraction between rotatable magnets in the magnet apparatus will not cause the magnets to rotate into an undesirable N-S orientation.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a plan view showing a conventional cochlear implant in an MRI magnetic field.

FIG. 2 is a partial section view of a conventional implant magnet apparatus and external magnet.

FIG. 3 is a partial section view of a conventional implant magnet apparatus.

FIG. 4 is a partial section view of a headpiece and an implanted cochlear implant with a conventional implant magnet apparatus.

FIG. 20 is a bottom plan view of a portion of the implant magnet apparatus illustrated in FIG. 14.

FIG. 21 is a perspective view of a portion of the implant magnet apparatus illustrated in FIG. 14.

FIG. 22 is a section view taken along line 22-22 in FIG. 14.

DETAILED DESCRIPTION OF THE EXEMPLARY EMBODIMENTS

Figure 5:
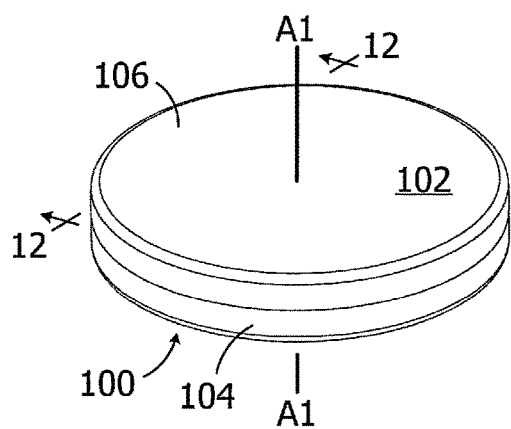
FIG. 5 is a perspective view of an implant magnet apparatus in accordance with one embodiment of a present invention.

The following is a detailed description of the best presently known modes of carrying out the inventions. This description is not to be taken in a limiting sense, but is made merely for the purpose of illustrating the general principles of the inventions.

As illustrated for example in FIGS. 5-9, an exemplary magnet apparatus 100 includes a case 102, with base 104 and a cover 106, a magnet frame 108, and a plurality of elongate diametrically magnetized magnets 110 within the frame that define a N-S direction. The exemplary case 102 is disk-shaped and defines a central axis A1, which is also the central axis of the magnet frame 108. The magnet frame 108 is freely rotatable relative to the case 102 about the central axis A1 over 360°. The magnets 110 rotate with the magnet frame 108 about the central axis A1. Each magnet 110 is also rotatable relative to the magnet frame 108 about its own longitudinal axis A2, with the frame limiting rotation to less than 360° in the manner described below with reference to FIGS. 10-12. The magnets 110 are also biased by the frame 108 in the manner described below to an at rest orientation relative to longitudinal axis A2 (FIGS. 6, 7 and 9) with enough force to prevent the magnetic attraction between the magnets from causing the magnets to rotate into N-S alignment with one another. The N-S orientation of the magnets 110 is, instead, parallel to the central axis A1 in the at rest orientation. In the illustrated implementation, the magnets 110 can rotate up to about 90° to 120° from the illustrated at rest orientation to, along with rotation about central axis A1, to bring the magnetic field of the magnets into alignment with a relatively strong external magnetic field (e.g., the MRI magnetic field discussed above). Once the external magnetic field is removed, the biasing force applied to the magnets 110 will return them to the at rest orientation.

To facilitate rotation of the magnet frame 108, lubricious material may be provided between the case 102 and the magnet frame 108. For example, in the illustrated embodiment, a pair of lubricious disks 112 and a lubricious ring 114 formed from polytetrafluoroethylene (PTFE) or other suitable materials are positioned between the case 102 and the magnet frame 108. In other implementations, a lubricious layer may be added to the inner surface of the case 102. The lubricious layer may be in the form of a specific finish of the inner surface that reduces friction, as compared to an unfinished surface, or may be a coating of a lubricious material such as PTFE, Parylene, or fluorinated ethylene propylene (FEP). In those instances where the base 104 and a cover 106 are formed by stamping, the finishing process may occur prior to stamping.

The exemplary case 102 is not limited to any particular configuration, size or shape. In the illustrated implementation, the case 102 is a two-part structure that includes the base 104 and the cover 106 which are secured to one another in such a manner that a hermetic seal is formed between the cover and the base. Suitable techniques for securing the cover 106 to the base 104 include, for example, seam welding with a laser welder. With respect to materials, the case 102 may be formed from biocompatible paramagnetic metals, such as titanium or titanium alloys, and/or biocompatible non-magnetic plastics such as polyether ether ketone (PEEK), low-density polyethylene (LDPE), high-density polyethylene (HDPE) and polyamide. In particular, exemplary metals include commercially pure titanium (e.g., Grade 2) and the titanium alloy Ti-6Al-4V (Grade 5), while exemplary metal thicknesses may range from 0.20 mm to 0.25 mm. With respect to size and shape, the case 102 may have an overall size and shape similar to that of conventional cochlear implant magnets so that the magnet apparatus 100 can be substituted for a conventional magnet in an otherwise conventional cochlear implant. In some implementations, the diameter that may range from 9 mm to 16 mm and the thickness may range from 1.5 mm to 3.0 mm. The diameter of the case 102 is 12.9 mm, and the thickness is 2.4 mm, in the illustrated embodiment.

Figure 6:
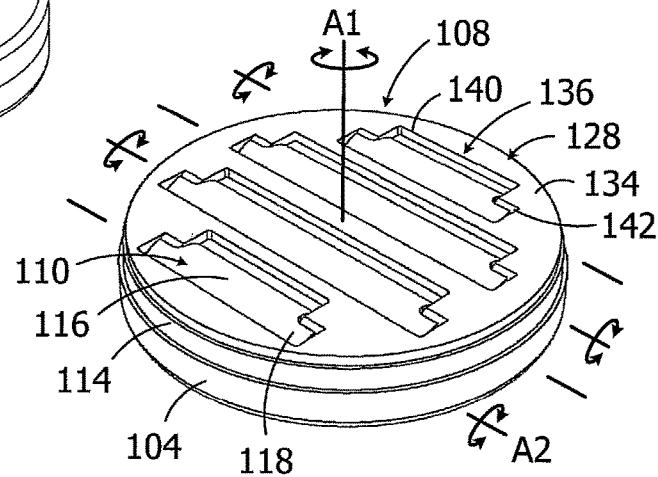
FIG. 6 is a perspective view of a portion of the implant magnet apparatus illustrated in FIG. 5.
Figure 7:
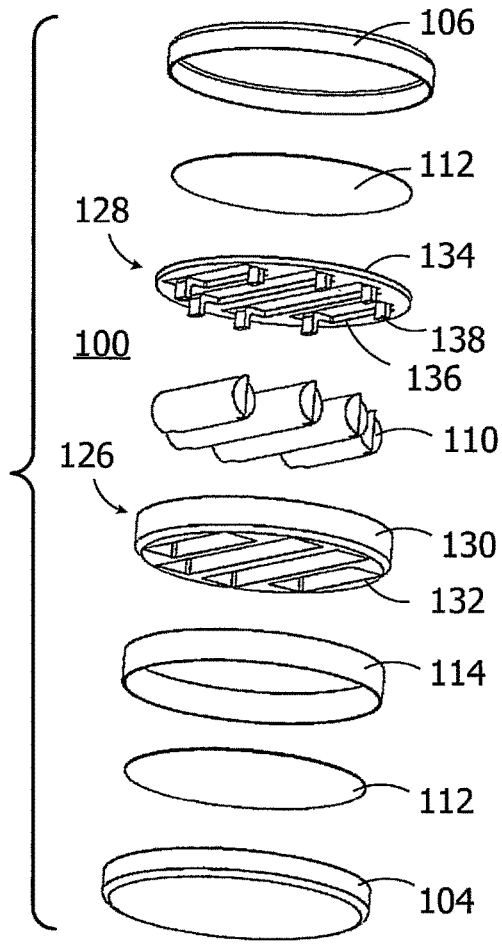
FIG. 7 is an exploded view of the implant magnet apparatus illustrated in FIG. 5.
Figure 8:
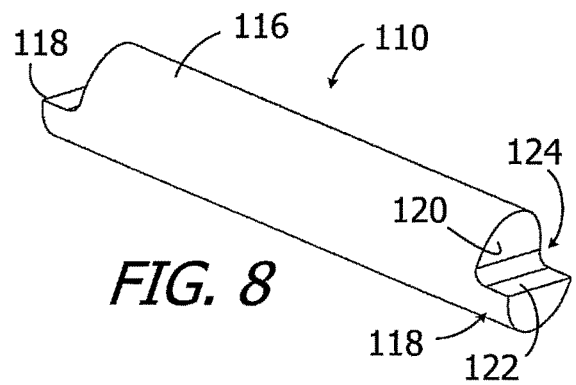
FIG. 8 is a perspective view of a portion of the implant magnet apparatus illustrated in FIG. 5.
Figure 9:
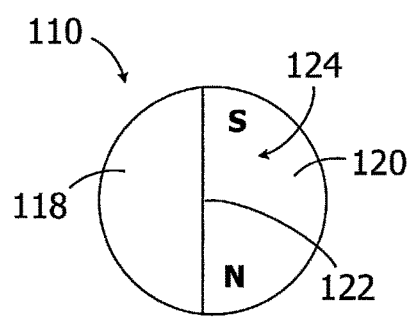
FIG. 9 is an end view of a portion of the implant magnet apparatus illustrated in FIG. 5.

Although the present inventions are not limited to any particular number, there are four elongate diametrically magnetized magnets 110 in the exemplary magnet apparatus 100. Two of the otherwise identical magnets 110 are relatively long and two are relatively short in order to efficiently utilize the available volume within the case 102, as is best shown in FIG. 6. The magnets 110 are also configured to be engaged by, and cooperate with, the biasing elements of the magnet frame 108 in the manner described below with reference to FIGS. 10-13. To that end, and referring to FIGS. 8 and 9, the exemplary magnets 110 each include a cylindrical body 116 and projections 118 at the longitudinal ends of the cylindrical body. The longitudinal ends of the cylindrical body 116 have an end wall 120, the projections 118 have a side wall 122. Recesses 124 are located adjacent to the end and side walls 120 and 122 at each longitudinal end. It should also be noted that the projection side walls 122 are parallel to the N-S orientation of the magnets 110. Suitable materials for the magnets 110 include, but are not limited to, neodymium-boron-iron and samarium-cobalt.

Figure 10:
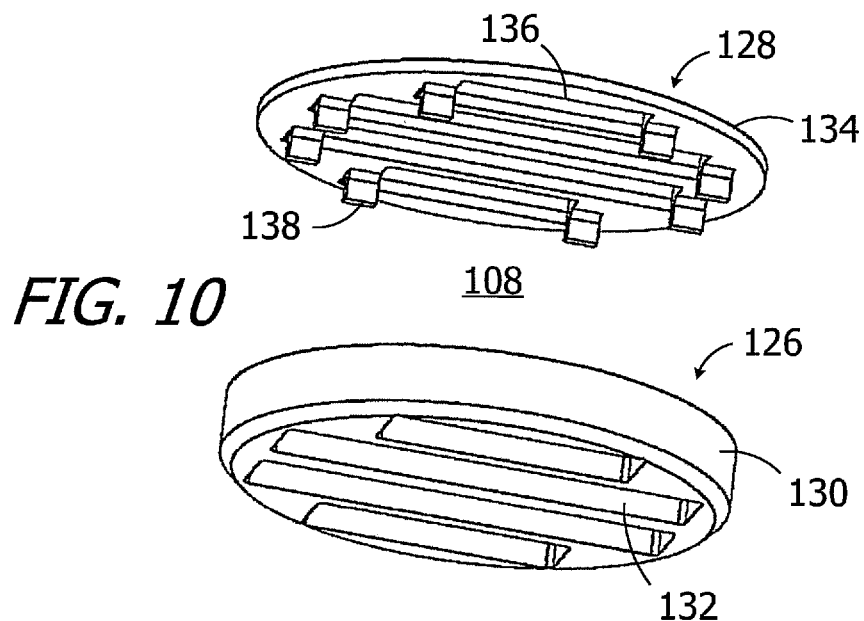
FIG. 10 is an exploded view of a portion of the implant magnet apparatus illustrated in FIG. 5.
Figure 11:
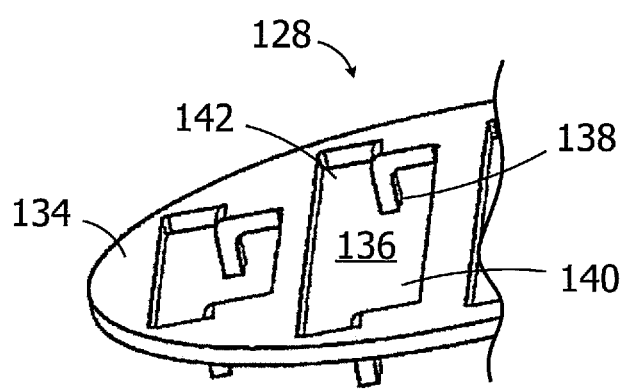
FIG. 11 is a perspective view of a portion of the implant magnet apparatus illustrated in FIG. 5.

Turning to FIGS. 10 and 11, the exemplary magnet frame 108 includes a base member 126 and a biasing member 128. The base member 126 includes a relatively thick disk 130 and a plurality of magnet receptacles 132 that extend through the disk 130. The biasing member 128 includes a relatively thin disk 134, a plurality of magnet apertures 136 that extend through the disk 134 and are aligned with the magnet receptacles 132, and a plurality of resilient elements 138 that are perpendicular to the disk 134 and that extend into the magnet receptacles 132. To accommodate the configuration of the magnets 110, the magnet apertures 136 each have a first portion 140 in which the magnet cylindrical body 116 is located as well as a pair of second portions 142 in which the magnet projections 118 are located. The magnet receptacles 132, which are rectangular in shape, have lengths that are equal to (or slightly greater than) the distance between the longitudinal ends of the magnets 110 and widths that are equal to (or slightly greater than) the diameter of the magnet cylindrical body 116. The combined thickness of the disks 130 and 134 are also equal to (or slightly greater than) the diameter of the magnet cylindrical body 116.

Figure 12:
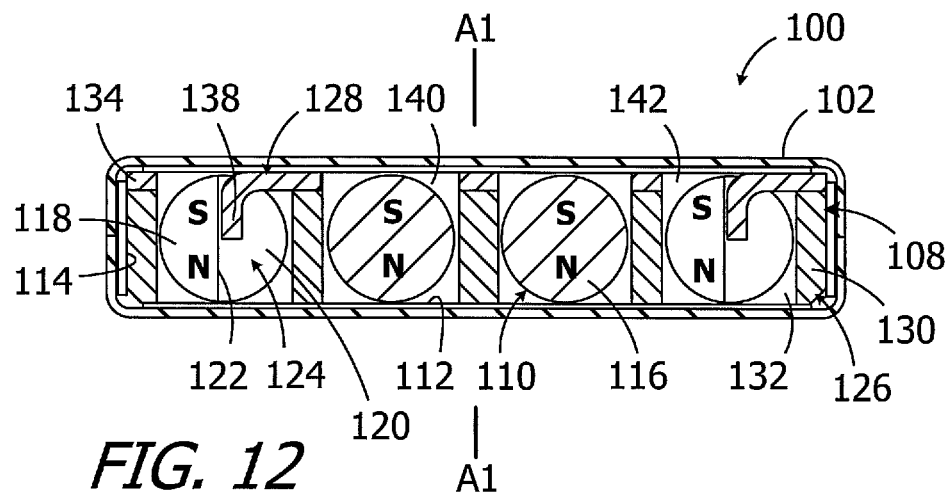
FIG. 12 is a section view taken along line 12-12 in FIG. 5.
Figure 13:
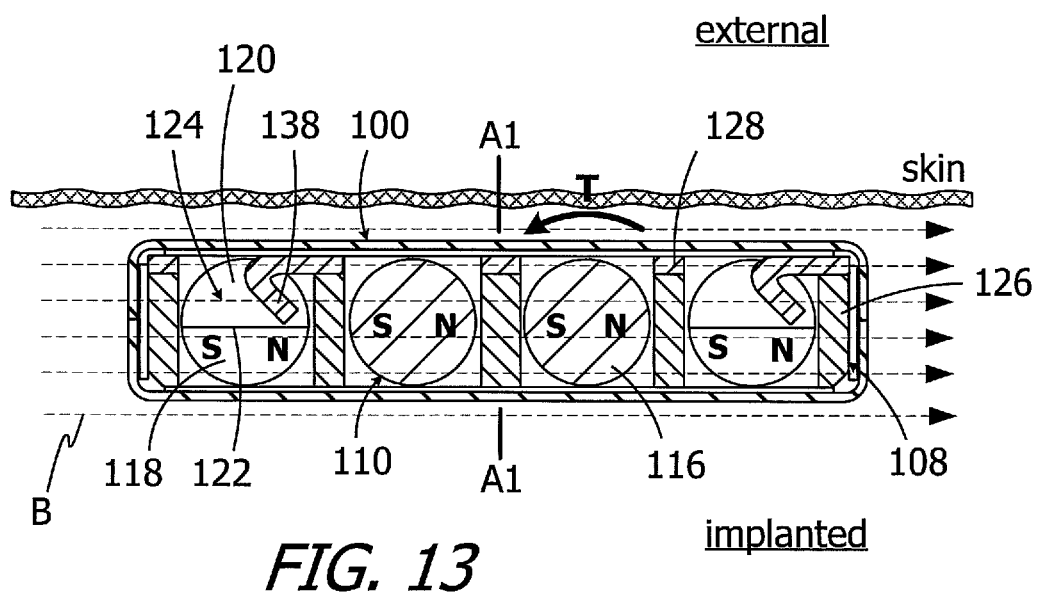
FIG. 13 is a section view similar to FIG. 12 with the magnets rotated.

As illustrated for example in FIG. 12, the respective configurations of the magnets 110 and the magnet frame 108, as well as the strength of the magnets 110 relative to the biasing force applied to the magnets by the magnet frame due to the stiffness of the resilient elements 138, results in the magnets being maintained in the orientation illustrated in FIG. 12. The N-S orientation of the magnets 110 is parallel to the central axis A1 of the magnet apparatus 100. In particular, the resilient elements 138 are within the recesses 124 and abut the side walls 122 of the projections 118 to prevent the magnets 110 from rotating into N-S alignment with one another. As such, the magnetic fields of the magnets 110 will be aligned with a headpiece magnet carried within a headpiece such that the N-S orientation of the headpiece magnet is perpendicular to the skin (note the magnet 26 of headpiece 30 in FIG. 4). Preferably, although not necessarily, the resilient elements will be no stiffer than is necessary to prevent the magnets from rotating into alignment with one another. When exposed to even a relatively weak a dominant MRI magnetic field B (e.g., an MRI magnetic field of 1.5 T or less, and in some instances, 0.3 T or less), however, the torque T on the magnets 110 will be sufficient to bend the resilient elements 138 and rotate the magnets about their axis A2 (FIG. 6), thereby aligning the magnetic fields of the magnets 110 with the MRI magnetic field B, as shown in FIG. 13. The magnet frame 108 will also rotate about axis A1 as necessary to align the magnetic fields of the magnets 110 with the MRI magnetic field B. When the magnet apparatus 100 is removed from the MRI magnetic field B, the resilient elements 138 will return to the unstressed state illustrated in FIG. 12, thereby rotating the magnets 110 back to the at rest orientation also illustrated in FIG. 12.

With respect to materials and manufacturing, suitable materials for the base member 126 and biasing member 128 of the magnet frame 108 include, but are not limited to, non-magnetic plastics such as PEEK, liquid crystal polymer (LCP), polyimide, and plastics reinforced with materials such as glass fibers, nylon, and carbon as well as paramagnetic superelastic metals such as nitinol. The base member 126 and biasing member 128, which may be formed by conventional molding and/or machining techniques, may be secured to one other by, for example, press-fit pins (not shown here) in the manner described below with reference to FIG. 25. In other implementations, magnet frame 108 may be formed as a one-piece structure with the features of the base member 126 and biasing member 128 incorporated therein.

Figure 14:
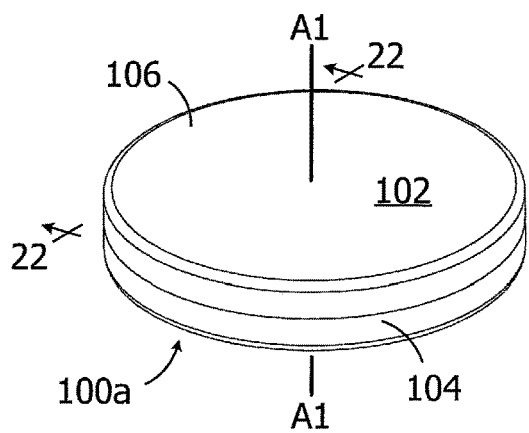
FIG. 14 is a perspective view of an implant magnet apparatus in accordance with one embodiment of a present invention.

Another exemplary magnet apparatus is generally represented by reference numeral 100*a* in FIG. 14. The magnet apparatus 100*a* is substantially similar to the magnet apparatus 100 illustrated in FIGS. 5-13 and similar elements are represented by similar reference numerals. For example, the magnet apparatus 100*a* includes the above-described case 102, a rotatable magnet frame, a plurality of magnets that are rotatable both with and relative to the magnet frame and are biased to a predetermined N-S orientation, and a pair of lubricious disks 112 and a lubricious ring 114 between the case and magnet frame. Here, however, the elongate diametrically magnetized magnets are biased to the predetermined N-S orientation by resilient element pairs, which are not integral with the remainder of the magnet frame, located at the longitudinal ends of the magnets.

Figure 15:
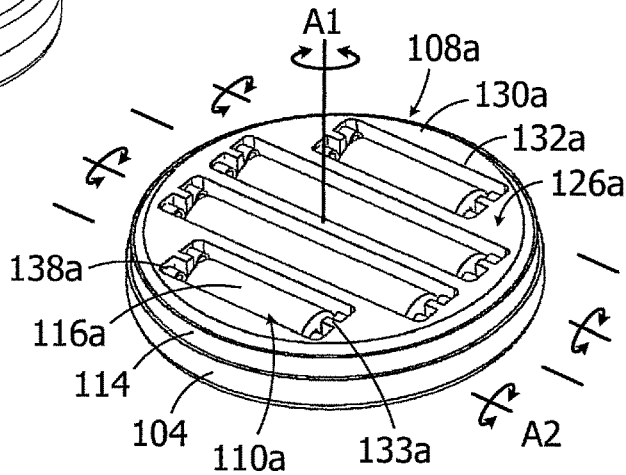
FIG. 15 is a perspective view of a portion of the implant magnet apparatus illustrated in FIG. 14.

Turning to FIG. 15, the magnet apparatus 100*a* includes a magnet frame 108*a* that is freely rotatable relative to the case 102 about the central axis A1 over 360°. The magnets 110*a* rotate with the magnet frame 108*a* about the central axis A1. Each magnet 110*a* is also rotatable relative to the magnet frame 108*a* about its own longitudinal axis A2, with the frame limiting rotation to less than 360° (e.g., about 90° to 120°), from the at rest orientation illustrated in FIGS. 15, 16, 20 and 22. The magnets 110*a* also biased by the frame 108*a* to an at rest orientation relative to longitudinal axis A2 (FIG. 22) with enough force to prevent the magnetic attraction between the magnets from causing the magnets to rotate into N-S alignment with one another. Such rotation about axis A1 and axis A2 brings the magnetic field of the magnets 110*a* into alignment with a relatively strong external magnetic field (e.g., the MRI magnetic field discussed above). Once the external magnetic field is removed, the biasing force applied to the magnets 110*a* will return them to the at rest orientation.

Figure 18:
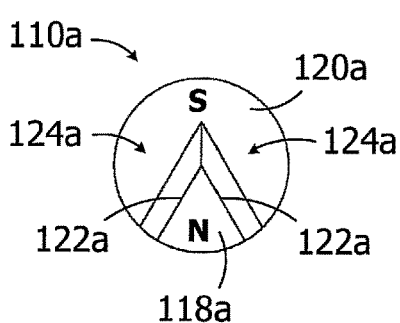
FIG. 18 is an end view of a portion of the implant magnet apparatus illustrated in FIG. 14.
Figure 19:
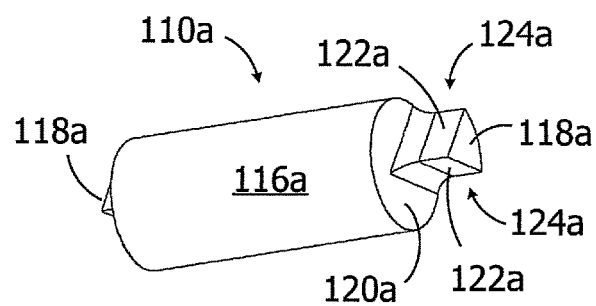
FIG. 19 is a perspective view of a portion of the implant magnet apparatus illustrated in FIG. 14.

As illustrated for example in FIGS. 18 and 19, the exemplary magnets 110*a* each include a cylindrical body 116*a* and projections 118*a* at the longitudinal ends of the cylindrical body. The longitudinal ends of the cylindrical body 116*a* have an end wall 120*a*. Each projection 118*a* has a pair of side walls 122*a*. Recesses 124*a* are located on opposite side of each projection 118*a* adjacent to the end wall 120*a* and side walls 122*a*.

Figure 16:
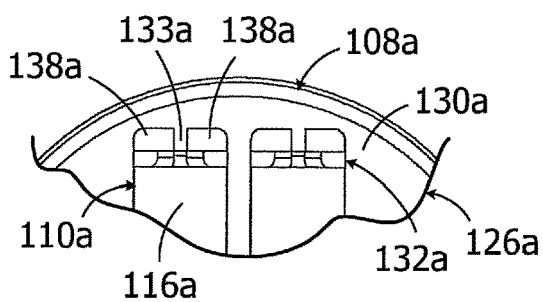
FIG. 16 is a plan view of a portion of the implant magnet apparatus illustrated in FIG. 14.
Figure 17:
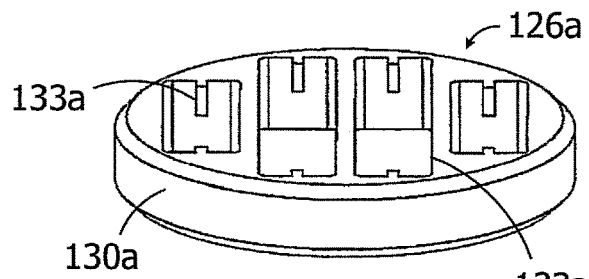
FIG. 17 is a perspective view of a portion of the implant magnet apparatus illustrated in FIG. 14.

The exemplary magnet frame 108*a* illustrated in FIGS. 15-17 has a base member 126*a* and a plurality of resilient elements 138*a*. The base member 126*a* includes a disk 130*a*, a plurality of magnet receptacles 132*a* that extend through the disk 130*a*, and support tabs 133*a* that are located at the longitudinal ends of each magnet receptacle. The narrow ends of the magnet projections 118*a* abut the support tabs (FIG. 22). The resilient elements 138*a*, which are described in greater detail below with reference to FIG. 21, are positioned within the magnet receptacles 132*a* on opposite sides of each support tab 133*a*. As such, there are four resilient elements 138*a* within each magnet receptacle 132*a*. The magnet receptacles 132*a*, which are rectangular in shape, have lengths that are equal to (or slightly greater than) the distance between the longitudinal ends of the magnets 110*a* as well as widths and thicknesses that are equal to (or slightly greater than) the diameter of the magnet cylindrical body 116*a*.

Turning to FIG. 21, the exemplary resilient elements 138*a* include an elliptical disk 134*a* with one or more aperture 136*a* that pass through the disk. The elliptical disk 134*a* is formed from a resilient material such as, for example, soft elastic rubber, silicone, and elastic porous plastics and other polymers. The thickness of the disk 134*a*, and the size, number and position of the apertures 136*a*, may be varied to achieve the desired resilient element stiffness.

As illustrated for example in FIG. 22, the respective configurations of the magnets 110*a* and the magnet frame 108*a*, as well as the strength of the magnets 110*a* relative to the stiffness of the resilient elements 138*a*, results in the magnets being maintained in the illustrated orientation. The N-S orientation of the magnets 110*a* is parallel to the central axis A1 of the magnet apparatus 100*a*. In particular, the resilient elements 138*a* are within the recesses 124*a* and abut the side walls 122*a* of the projections 118*a* to prevent the magnets 110*a* from rotating into N-S alignment with one another. When exposed to a dominant MRI magnetic field (not shown), however, the torque on the magnets 110*a* will be sufficient to compress one of the resilient elements 138*a* at each magnet end so that the magnets can rotate about their axis A2 (FIG. 15) in the manner described above with reference to FIG. 13. The magnet frame 108*a* will also rotate as necessary to align the magnetic fields of the magnets 110*a* with the MRI magnetic field. When the magnet apparatus 100*a* is removed from the MRI magnetic field, the resilient elements 138*a* will return to the unstressed state illustrated in FIG. 22, thereby rotating the magnets 110*a* back to the at rest orientation.

Figure 23:
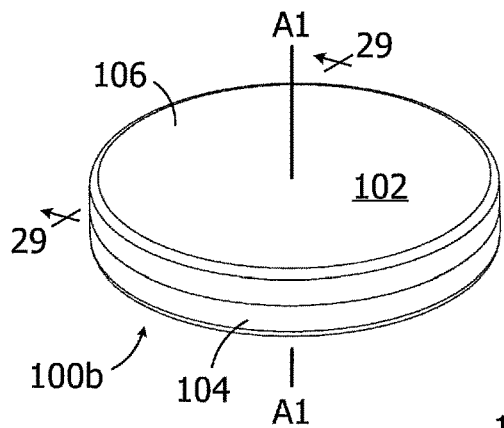
FIG. 23 is a perspective view of an implant magnet apparatus in accordance with one embodiment of a present invention.

Another exemplary magnet apparatus is generally represented by reference numeral 100*b* in FIG. 23. The magnet apparatus 100*b* is substantially similar to the magnet apparatus 100 (FIGS. 5-13) and the magnet apparatus 100*a* (FIGS. 14-22) and similar elements are represented by similar reference numerals. For example, the magnet apparatus 100*b* includes the above-described case 102, a rotatable magnet frame, a plurality of magnets that are rotatable both with and relative to the magnet frame and are biased to a predetermined N-S orientation, a pair of lubricious disks 112, and a lubricious ring 114. Here, however, the elongate diametrically magnetized magnets are biased to the predetermined N-S orientation by resilient elements that are perpendicular to axis A1.

Figure 24:
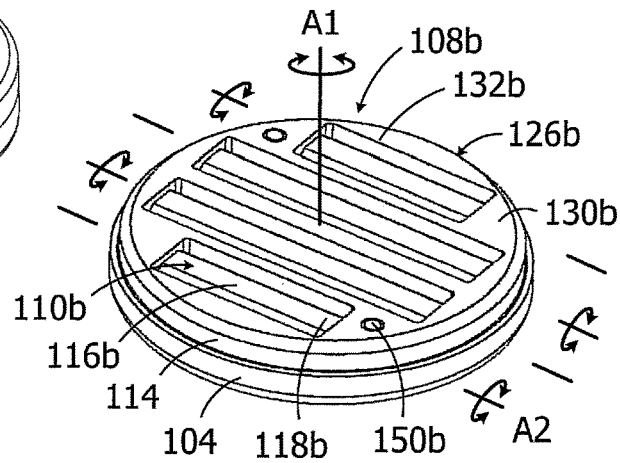
FIG. 24 is a perspective view of a portion of the implant magnet apparatus illustrated in FIG. 23.

Turning to FIG. 24, the magnet apparatus 100*b* includes a magnet frame 108*b* that is freely rotatable relative to the case 102 about the central axis A1 over 360°. The magnets 110*b* rotate with the magnet frame 108*b* about the central axis A1. Each magnet 110*b* is also rotatable relative to the magnet frame 108*a* about its own longitudinal axis A2, with the frame limiting rotation to less than 360° (e.g., about 90° to 120°) from the at rest orientation illustrated in FIGS. 24, 25 and 29. The magnets 110*b* also biased by the frame 108*b* to an at rest orientation relative to longitudinal axis A2 with enough force to prevent the magnetic attraction between the magnets from causing the magnets to rotate into N-S alignment with one another. Such rotation about axis A1 and axis A2 brings the magnetic field of the magnets 110*b* into alignment with a relatively strong external magnetic field (e.g., the MRI magnetic field discussed above). Once the external magnetic field is removed, the biasing force applied to the magnets 110*b* will return them to the at rest orientation.

Figure 26:
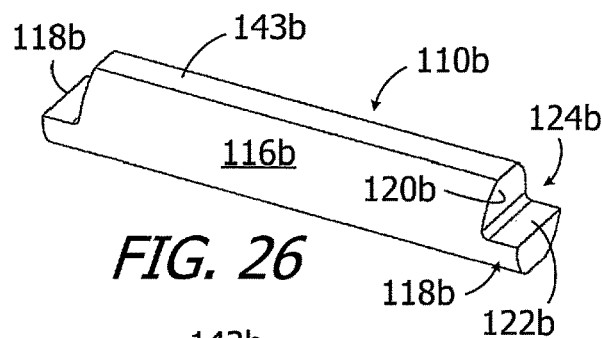
FIG. 26 is a perspective view of a portion of the implant magnet apparatus illustrated in FIG. 23.
Figure 27:
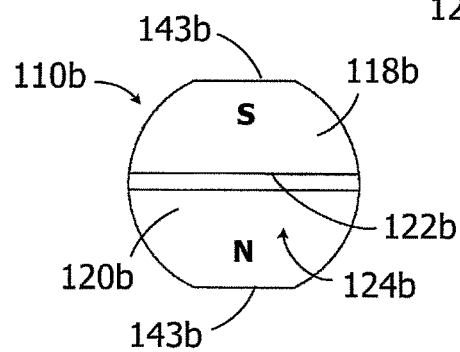
FIG. 27 is an end view of a portion of the implant magnet apparatus illustrated in FIG. 23.

As illustrated for example in FIGS. 26 and 27, the exemplary magnets 110b each include a cylindrical body 116b and projections 118b at the longitudinal ends of the cylindrical body. The longitudinal ends of the cylindrical body 116b also have an end wall 120b, and each projection 118b has a bottom wall 122b that is perpendicular to the N-S orientation of the magnet 110b. A recess 124b is located at each projection 118b between the adjacent end wall 120b and bottom wall 122b. The exemplary magnets 110b also include flat portions 143b that are located radially inwardly from the circular perimeter (in a plane perpendicular to axis A2) defined by the remainder of the cylindrical body 116b. Put another way, the non-circular outer perimeter of the magnet main body 116b (in a plane perpendicular to axis A2) includes, for example, two semi-circular portions and two flat portions that extend from one semi-circular portion to the other. As is discussed in greater detail below with reference to FIG. 29, the flat portions 143b create a gap between the magnets 110b and the inner surface of the case 102 (or lubricious disks 112 if present) to reduce the likelihood of damage to the magnets.

Figure 25:
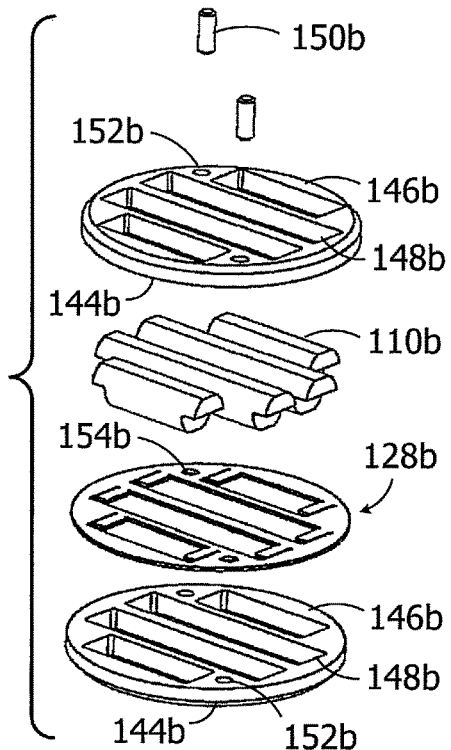
FIG. 25 is an exploded view of a portion of the implant magnet apparatus illustrated in FIG. 23.
Figure 28:
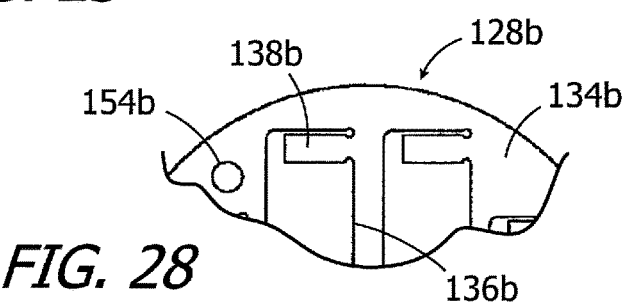
FIG. 28 is a plan view of a portion of the implant magnet apparatus illustrated in FIG. 23.

The exemplary magnet frame 108b illustrated in FIGS. 24, 25 and 28 has a base member 126b and a biasing member 128b. The base member 126b, which includes a relatively thick disk 130b and a plurality of magnet receptacles 132b that extend through the disk 130b, is a two-part structure that is formed by a pair of base sub-members 144b. The magnet receptacles 132b, which are rectangular in shape, have lengths that are equal to (or slightly greater than) the distance between the longitudinal ends of the magnets 110b as well as widths and thicknesses that are equal to (or slightly greater than) the diameter of the magnet cylindrical body 116b. Each sub-member 144b has a disk 146b and a plurality of apertures 148b. The biasing member 128b, which is sandwiched between the base sub-members 144b, includes a relatively thin disk 134b, a plurality of magnet apertures 136b that extend through the disk 134 and are aligned with the magnet receptacles 132b, and a plurality of resilient elements 138b that are coplanar with the disk 134b and that extend into the magnet receptacles 132b. The biasing member 128b and the base sub-members 144b may be held together with press-fit pins 150b (e.g., titanium or stainless steel pins) that extend through apertures 152b and 154b.

Figure 29:
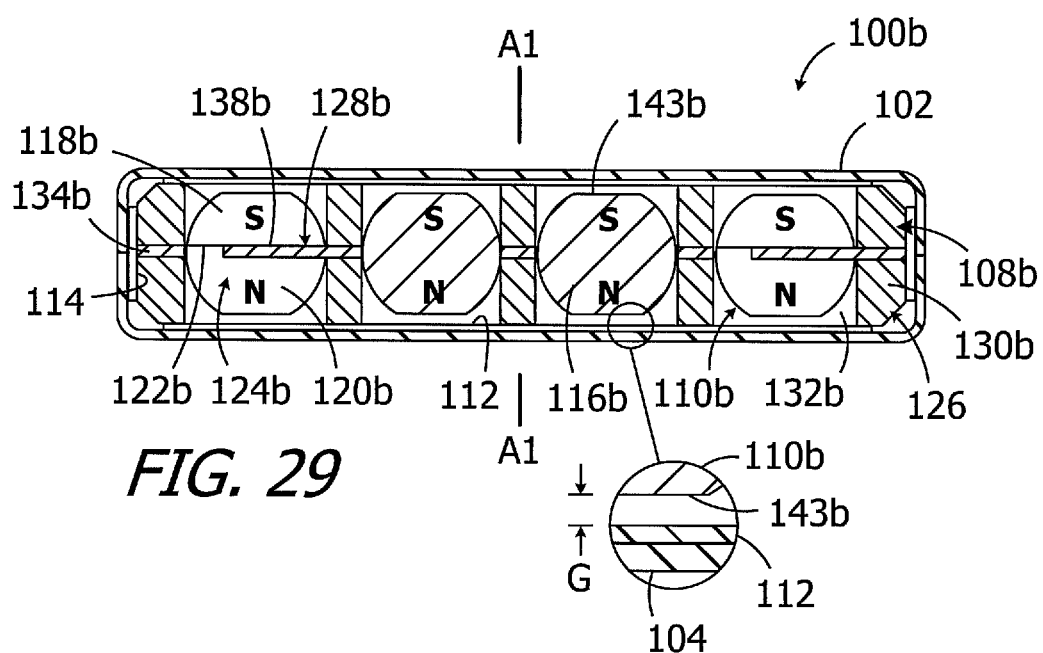
FIG. 29 is a section view taken along line 29-29 in FIG. 23.

As illustrated for example in FIG. 29, the aforementioned flat portions 143b, the relative sizes of the case 102 and magnets 110b, and the manner in which the magnet projections 118b rest on the resilient elements 138b together result in gaps G being located between the magnets and the upper and lower inner surfaces of the case 102 (or the inner surfaces of the lubricious disks 112 if present). The gaps G prevent forces that may deflect the case 102 from reaching the magnets 110b, thereby preventing damage to the magnets.

Figure 30:
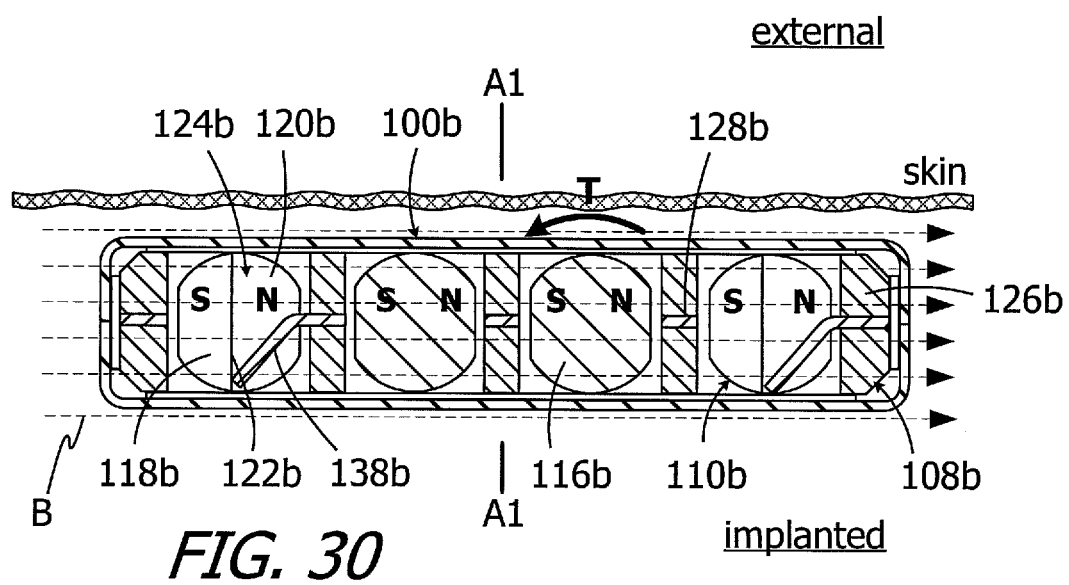
FIG. 30 is a section view similar to FIG. 29 with the magnets rotated.

The respective configurations of the magnets 110b and the magnet frame 108b, as well as the strength of the magnets 110b relative to the stiffness of the resilient elements 138b, results in the magnets being maintained in the orientation illustrated in FIG. 29. The N-S orientation of the magnets 110b is parallel to the central axis A1 of the magnet apparatus 100b. In particular, the resilient elements 138b are within the recesses 124b and abut the bottom walls 122b of the projections 118b to prevent the magnets 110b from rotating into N-S alignment with one another. As such, the magnetic fields of the magnets 110b will be aligned with a headpiece magnet carried within a headpiece such that the N-S orientation of the headpiece magnet is perpendicular to the skin (note the magnet 26 of headpiece 30 in FIG. 4). When exposed to a dominant MRI magnetic field B, however, the torque T on the magnets 110b will be sufficient to bend the resilient elements 138b and rotate the magnets about their axis A2 (FIG. 24), thereby aligning the magnetic fields of the magnets 110 with the MRI magnetic field B, as shown in FIG. 30. The magnet frame 108b will also rotate about axis A1 as necessary to align the magnetic fields of the magnets 110b with the MRI magnetic field B. When the magnet apparatus 100b is removed from the MRI magnetic field B, the resilient elements 138b will return to the unstressed state illustrated in FIG. 29, thereby rotating the magnets 110b back to the at rest orientation.

Figure 31:
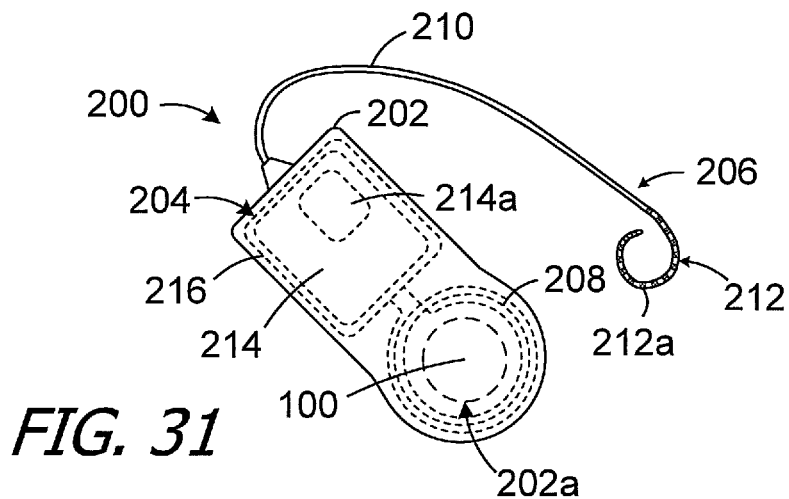
FIG. 31 is a plan view of a cochlear implant in accordance with one embodiment of a present invention.

One example of a cochlear implant (or "implantable cochlear stimulator") including the present magnet apparatus 100 (or 100a or 100b) is the cochlear implant 200 illustrated in FIG. 31. The cochlear implant 200 includes a flexible housing 202 formed from a silicone elastomer or other suitable material, a processor assembly 204, a cochlear lead 206, and an antenna 208 that may be used to receive data and power by way of an external antenna that is associated with, for example, a sound processor unit. The cochlear lead 206 may include a flexible body 210, an electrode array 212 at one end of the flexible body, and a plurality of wires (not shown) that extend through the flexible body from the electrodes 212a (e.g., platinum electrodes) in the array 212 to the other end of the flexible body. The magnet apparatus 100 is located within a region encircled by the antenna 208 (e.g., within an internal pocket 202a defined by the housing 202) and insures that an external antenna (discussed below) will be properly positioned relative to the antenna 208. The exemplary processor assembly 204, which is connected to the electrode array 212 and antenna 208, includes a printed circuit board 214 with a stimulation processor 214a that is located within a hermetically sealed case 216. The stimulation processor 214a converts the stimulation data into stimulation signals that stimulate the electrodes 212a of the electrode array 212.

Figure 32:
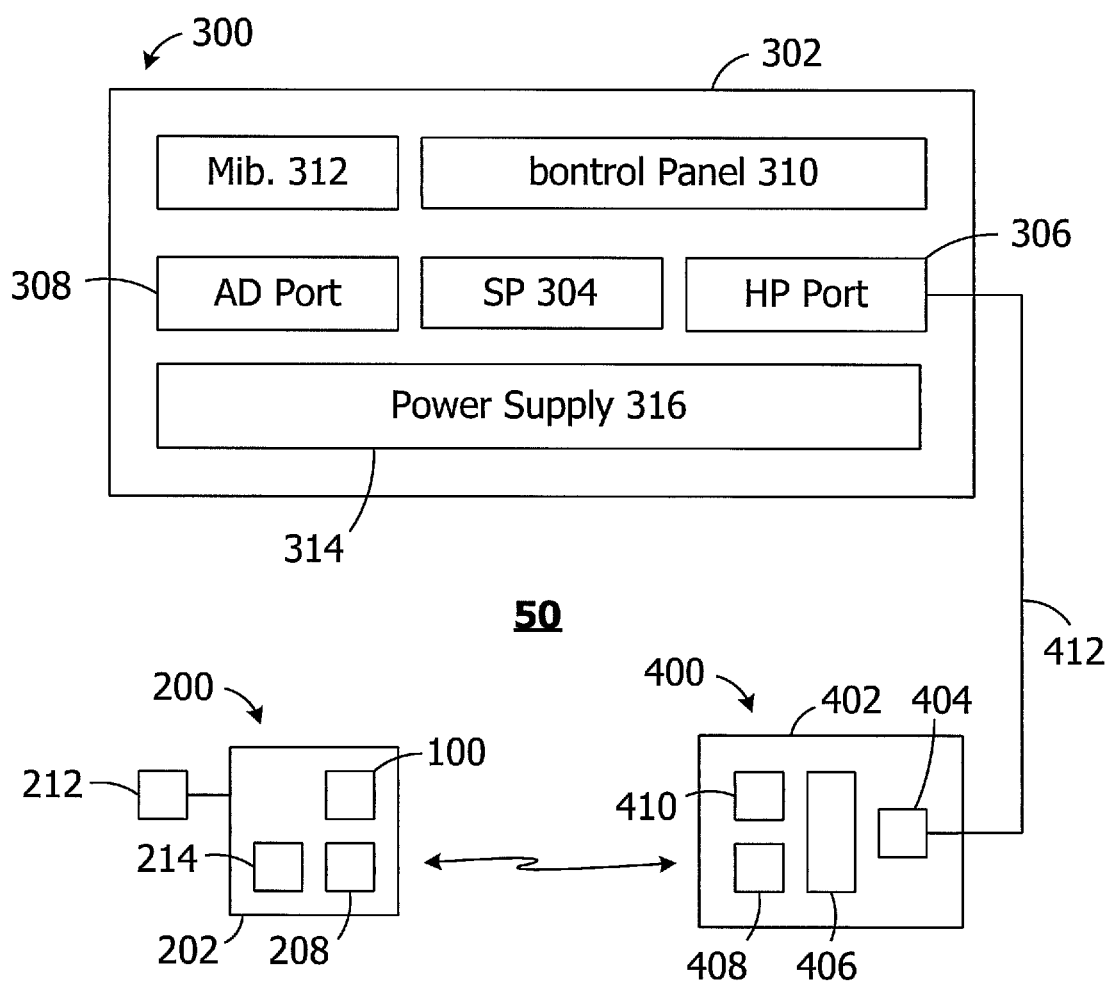
FIG. 32 is a block diagram of a cochlear implant system in accordance with one embodiment of a present invention.

Turning to FIG. 32, the exemplary cochlear implant system 50 includes the cochlear implant 200, a sound processor, such as the illustrated body worn sound processor 300 or a behind-the-ear sound processor, and a headpiece 400.

The exemplary body worn sound processor 300 in the exemplary ICS system 50 includes a housing 302 in which and/or on which various components are supported. Such components may include, but are not limited to, sound processor circuitry 304, a headpiece port 306, an auxiliary device port 308 for an auxiliary device such as a mobile phone or a music player, a control panel 310, one or more microphones 312, and a power supply receptacle 314 for a removable battery or other removable power supply 316 (e.g., rechargeable and disposable batteries or other electrochemical cells). The sound processor circuitry 304 converts electrical signals from the microphone 312 into stimulation data. The exemplary headpiece 400 includes a housing 402 and various components, e.g., a RF connector 404, a microphone 406, an antenna (or other transmitter) 408 and a positioning magnet apparatus 410, that are carried by the housing. The magnet apparatus 410 may consist of a single magnet or one or more magnets and a shim. The headpiece 400 may be connected to the sound processor headpiece port 306 by a cable 412. The positioning magnet apparatus 410 is attracted to the magnet apparatus 100 of the cochlear stimulator 200, thereby aligning the antenna 408 with the antenna 208. The stimulation data and, in many instances power, is supplied to the headpiece 400. The headpiece 400 transcutaneously transmits the stimulation data, and in many instances power, to the cochlear implant 200 by way of a wireless link between the antennae. The stimulation processor 214a converts the stimulation data into stimulation signals that stimulate the electrodes 212a of the electrode array 212.

In at least some implementations, the cable 412 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 312 on the sound processor 300, the microphone 406 may be also be omitted in some instances. The functionality of the sound processor 300 and headpiece 400 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. By way of example, but not limitation, magnets may be provided with a single projection. The inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant, comprising:
a cochlear lead including a plurality of electrodes;
an antenna;
a stimulation processor operably connected to the antenna and to the cochlear lead; and
a magnet apparatus, adjacent to the antenna, including a case defining a central axis, a magnet frame within the case and rotatable relative to the case about the central axis of the case, and a plurality of diametrically magnetized magnets that are located in the magnet frame, the magnets each defining a respective longitudinal axis and a respective N-S direction and being rotatable about the longitudinal axis relative to the magnet frame and biased by the magnet frame to a respective predetermined N-S rotational orientation.

2. A cochlear implant as claimed in claim 1, wherein the predetermined N-S rotational orientation of the magnets is parallel to the central axis of the case.

3. A cochlear implant as claimed in claim 1, wherein the predetermined N-S rotational orientation of the magnets is such that the N-S directions of the magnets are parallel to one another.

4. A cochlear implant as claimed in claim 1, wherein the magnets include a main body, defining longitudinal ends and a circular cross-section in a plane perpendicular to the longitudinal axis, and a projection at each longitudinal end.

5. A cochlear implant as claimed in claim 1, wherein the magnets include a main body, defining longitudinal ends and a non-circular cross-section in a plane perpendicular to the longitudinal axis, and a projection at each longitudinal end.

6. A cochlear implant as claimed in claim 1, further comprising:
lubricious material between the case and the magnet frame.

7. A cochlear implant as claimed in claim 1, wherein the antenna, the stimulation processor and the magnet apparatus are located within a flexible housing.

8. A cochlear implant as claimed in claim 1, wherein the magnets define a magnetic field; and
the magnet frame applies a biasing force to the magnets that is insufficient to prevent rotation of the magnets in response to the presence of an MRI magnetic field that is perpendicular to the magnetic field of the magnets.

9. A system, comprising
a cochlear implant as claimed in claim 1; and
a headpiece including
an antenna, and
a headpiece magnet apparatus associated with the antenna.

10. A cochlear implant, comprising:
a cochlear lead including a plurality of electrodes;
an antenna;
a stimulation processor operably connected to the antenna and to the cochlear lead; and
a magnet apparatus, adjacent to the antenna, including a case defining a central axis, a magnet frame within the case and rotatable about the central axis of the case, and a plurality of diametrically magnetized magnets that are located in the magnet frame, the magnets each defining a respective longitudinal axis and a respective N-S direction and being rotatable about the longitudinal axis relative to the magnet frame and biased by the magnet frame to a respective predetermined N-S rotational orientation;
wherein
the magnets define first and second longitudinal ends and at least one of the longitudinal ends includes a projection; and
the frame includes a plurality of magnet receptacles in which the magnets are respectively located and a plurality of resilient elements that engage the projections to bias the magnets to the predetermined N-S rotational orientation.

11. A cochlear implant as claimed in claim 10, wherein the magnets include a projection at each longitudinal end.

12. A cochlear implant as claimed in claim 10, wherein the projections include a surface that is perpendicular to the N-S direction of the magnet; and
the resilient elements extend in a direction that is perpendicular to the central axis of the case and engage the surface.

13. A cochlear implant as claimed in claim 10, wherein a pair of resilient elements engages each projection.

14. A cochlear implant as claimed in claim 10, wherein the resilient elements are formed from superelastic metal.

15. A method, comprising:
in an implantable cochlear stimulator including an antenna and a magnet apparatus, adjacent to the antenna, having a case that defines a central axis, a magnet frame within the case and rotatable relative to the case about the central axis of the case, and a plurality of diametrically magnetized magnets that define a longitudinal axis and a N-S direction and are located in the magnet frame and rotatable about the longitudinal axis relative to the magnet frame, the step of biasing the magnets to a predetermined N-S rotational orientation where the N-S directions are not perpendicular to the central axis of the case.

16. A method as claimed in claim 15, further comprising the step of:
allowing the magnets to rotate out of the predetermined N-S rotational orientation in response to an application of an MRI magnetic field.

17. A method as claimed in claim 16, wherein
the MRI magnetic field has a magnetic flux density of less than 1.5 Tesla.

18. A method as claimed in claim 15, wherein
the frame biases the magnets to the predetermined N-S rotational orientation.

19. A method as claimed in claim 15, wherein
the predetermined N-S rotational orientation is parallel to the central axis of the case.

* * * * *